US005167225A

United States Patent [19]

Cheng-I

[11] Patent Number: 5,167,225

[45] Date of Patent: Dec. 1, 1992

[54] MULTI-POINTED AUTOMATIC SOLE MASSAGER

[76] Inventor: Cheng Cheng-I, No. 19, Tong Yuan Road, Chung Li Industrial Park, Taiwan

[21] Appl. No.: 748,451

[22] Filed: Aug. 22, 1991

[51] Int. Cl.[5] .......... A61N 7/00

[52] U.S. Cl. .......... 128/44; 128/52; 128/66

[58] Field of Search .......... 328/32, 36, 52, 44, 328/51, 59-62 R; 128/52, 65, 66

[56] References Cited

U.S. PATENT DOCUMENTS

| | | | |
|---|---|---|---|
| 2,153,230 | 4/1939 | Bagnell | 128/52 |
| 3,626,933 | 12/1971 | Pollock | 128/52 |
| 4,085,738 | 4/1978 | Kodera | 128/52 X |
| 4,291,685 | 9/1981 | Taelman | 128/32 X |
| 4,414,963 | 11/1983 | Kunz | 128/60 |
| 4,493,315 | 1/1985 | Iwahashi | 128/60 |
| 4,777,945 | 10/1988 | Curtaz et al. | 128/52 |
| 4,852,553 | 8/1989 | Voykin | 128/25 B |
| 4,856,496 | 8/1989 | Chursinoff | 128/52 |

*Primary Examiner*—Robert A. Hafer
*Assistant Examiner*—Brian E. Hanlon
*Attorney, Agent, or Firm*—Morton J. Rosenberg; David I. Klein

[57] ABSTRACT

The multi-pointed automatic sole massager includes a pair of foot receiving receptacles having a plurality of vertically moving rods with removable massage heads provided for massaging the sole of a human foot. Each rod is moved vertically by a rotating disk member having a plurality of ridges on its upper surface. As the disk member is rotated, the massage heads exert pressure against accupressure points on the sole of the foot. Each foot receptacle is provided with a plurality of guide openings positioned at locations which correspond to known accupressure points in the sole of the human foot. An evaporator mounted to the massager supplies therapeutic vapors to the sole of the user's foot through the guide openings and to an elongated flexible conduit for directing the therapeutic vapors to other parts of the user's body.

2 Claims, 6 Drawing Sheets

MULTI-POINTED AUTOMATIC SOLE MASSAGER

BACKGROUND OF THE INVENTION

The present invention relates to a massager for the sole of a foot. The multi-pointed automatic sole massager is provided with foot receptacles having a plurality of removable massaging heads strategically located to engage the pressure points on the sole of a human foot. Each removable massaging head is disposed on a vertically displaceable elongated rod. The lower end of each rod contiguously contacts an upper end of a rotating disk. As the disk rotates, ridges on its upper surface force the rods to move in a vertical direction. The present invention also includes means for providing a therapeutic fluid to the foot receptacles and to other parts of the user's body.

The sole of the human foot has a number of accupressure points. Prior art sole massagers generally provide constant pressure to the entire sole or general areas of the sole of a user's foot. However, such prior art devices do not provide the relief and therapeutic effects sought by the user. Constant pressure applied to the entire sole of the foot does not soothe the sole or provide relief or relieve any pain on parts of the body that correlate to accupressure points and the sole. Thus, prior art devices which provide pressure to the entire sole of the foot fail to efficiently and thoroughly stimulate individual accupressure points in the sole. Additionally, prior art sole massagers have not included means to provide a therapeutic fluid to the soles and to other parts of the user's body.

There still remains a need for a sole massager that will effectively stimulate specific accupressure points in the soles of human feet and provide a therapeutic fluid to the soles of the feet and to other parts of a user's body.

SUMMARY OF THE INVENTION

It is a primary object of the present invention to provide a multi-pointed sole massager with a set of massaging rods to stimulate all the accupressure points in the sole of the human foot without having to apply pressure to the entire sole of the user's foot. A second object of the present invention is to stimulate all sole accupressure points automatically in a scanning mode. The third object of the present invention is to provide in-depth stimulation of the roots of the sole accupressure points through the pressure of a user's body weight exerted on a vertically moving massaging rod driven by a motor through reducing gears. A fourth object of the present invention is to provide a therapeutic fluid generated from a medicinal evaporator built in the sole massager as another stimulant to the sole accupressure points. A fifth object of the present invention is to provide a therapeutic fluid to parts of the user's body other than the soles of the feet. Another object of the present invention is to provide removable massaging heads that can be replaced and changed with respect to sizes, shapes, and materials. Still another object of the present invention is to provide massaging rods which can be vertically adjusted to accommodate different individuals.

DESCRIPTION OF THE PREFERRED EMBODIMENTS

Figure 1:
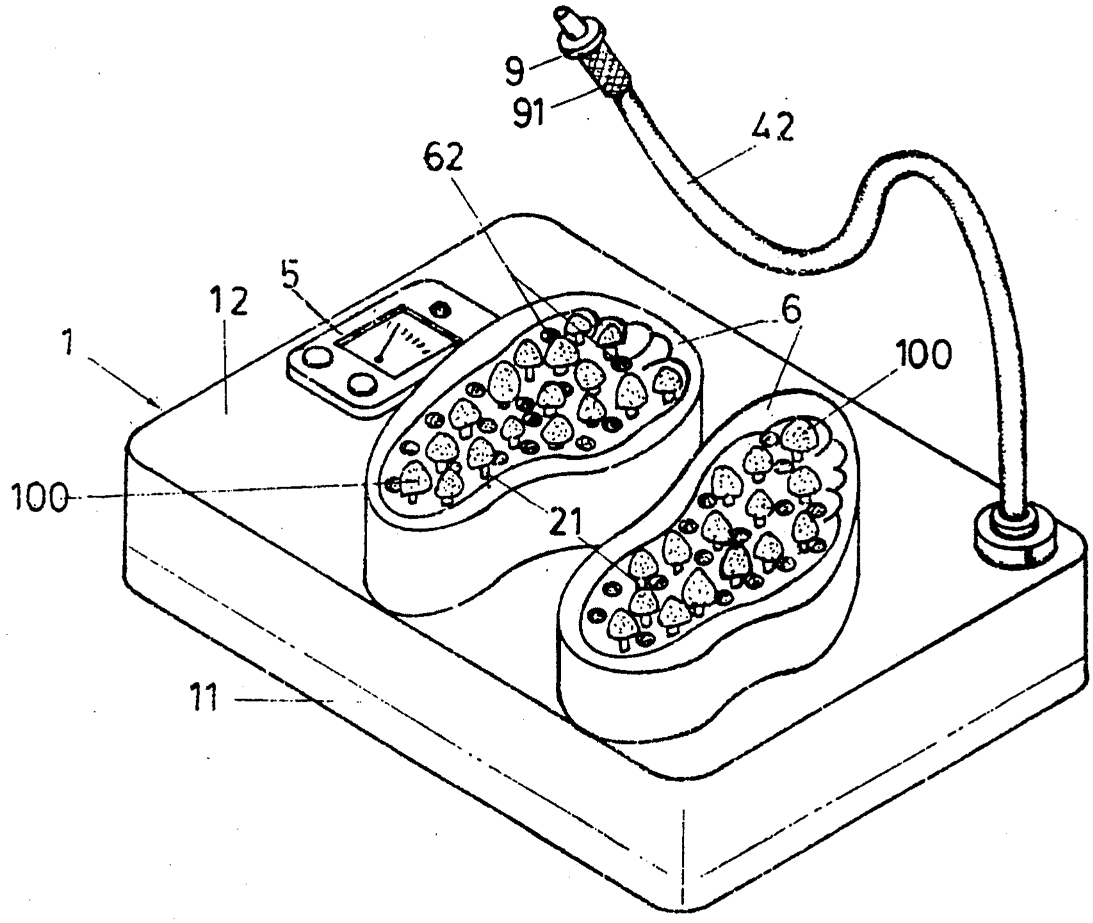
FIG. 1 is a perspective view of the preferred housing structure of the invention.
Figure 2:
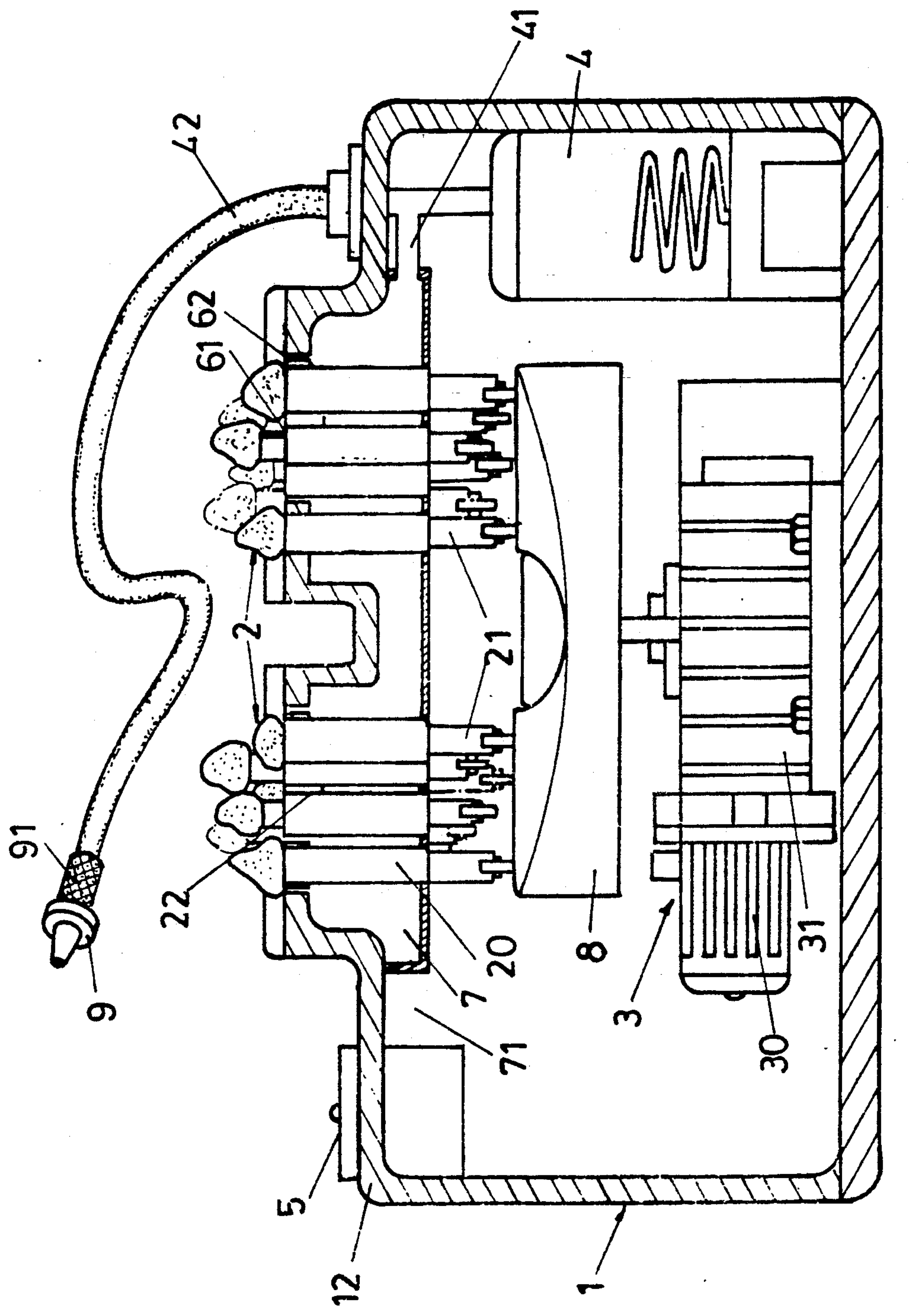
FIG. 2 is a cross-sectional view of the preferred housing structure of the invention and the parts/components therein.

Referring to FIGS. 1 and 2, the multi-pointed automatic sole massager comprises a housing 1, a pair of foot receptacles integrally connected to and extending upwardly from the housing 1, a plurality of through guide openings 62 disposed in the housing 1, a first plurality of through openings 64 disposed in the housing 1 between adjacent through guide openings 62, a plurality of elongated rod members 21 disposed in the through openings 64, a drive means 3 for vertically displacing elongated rod members 21, an elongated flexible conduit 42 mounted to the housing 1, means for providing a therapeutic fluid to the foot receptacle 6 and to the flexible conduit 42, and means for controlling the drive means 3 and a power source (not shown).

Figure 3:
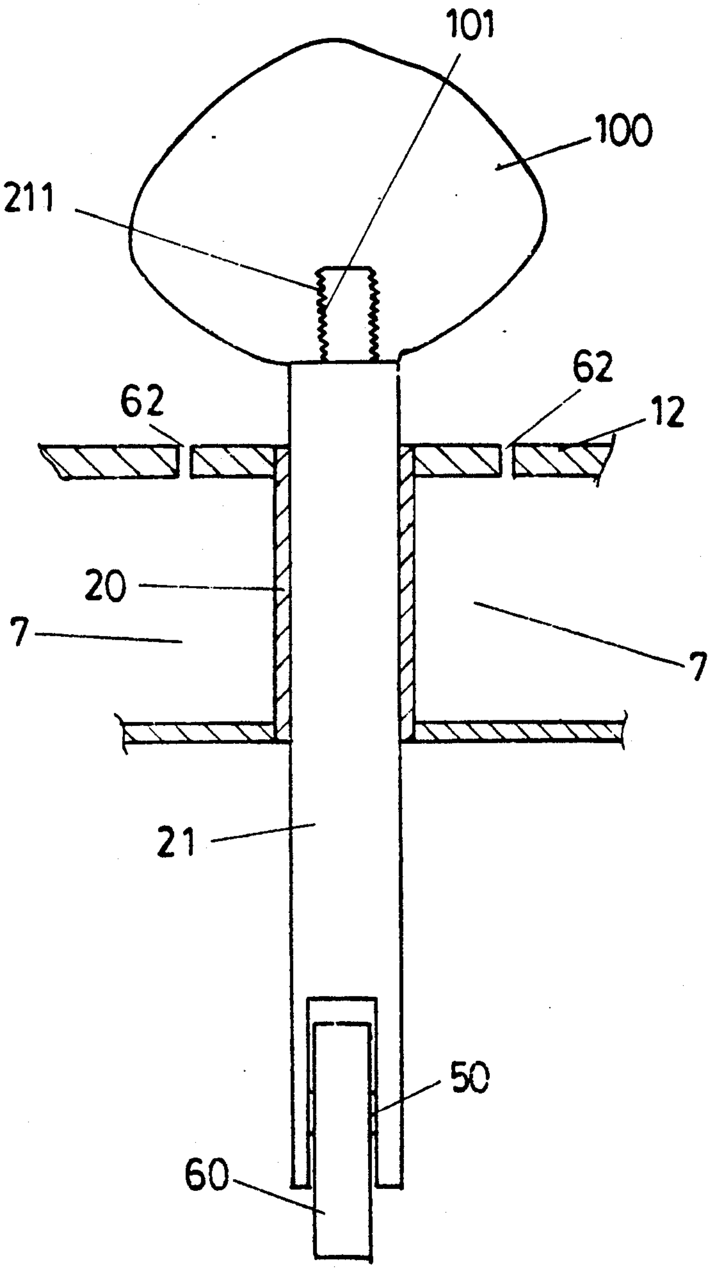
FIG. 3 is a cross-sectional view of the assembly of the massaging rod of the invention.
Figure 4B:
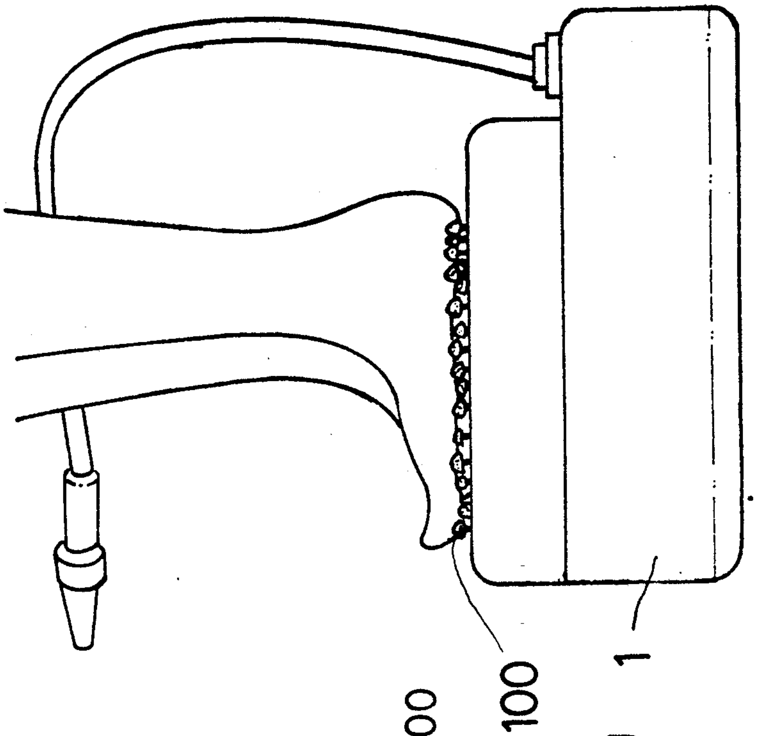
FIG. 4 (A,B) are profile illustrations of a user's foot being massaged by the invention.
Figure 4A:
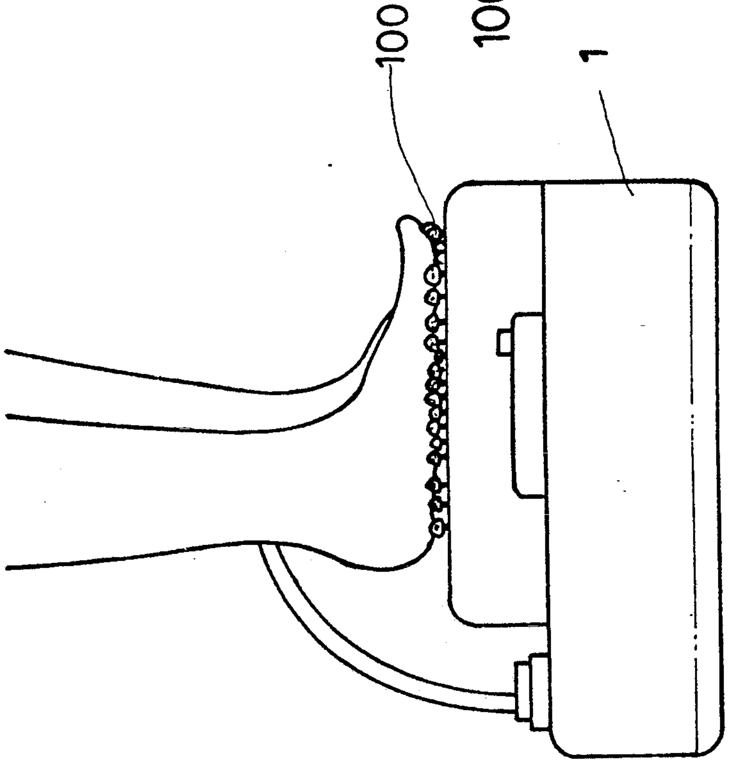
Figure 5A:
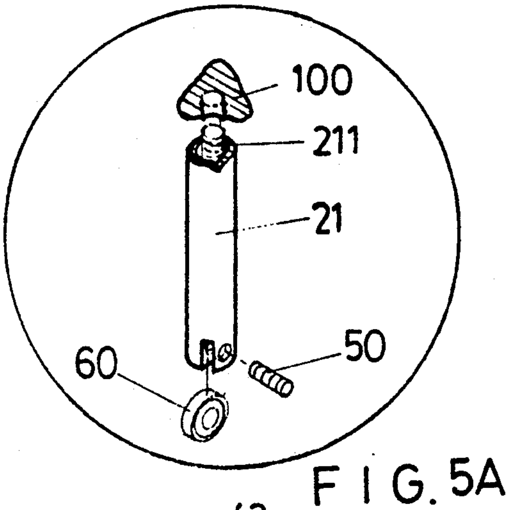
FIG. 5A is a perspective view of the massaging rod.
Figure 5:
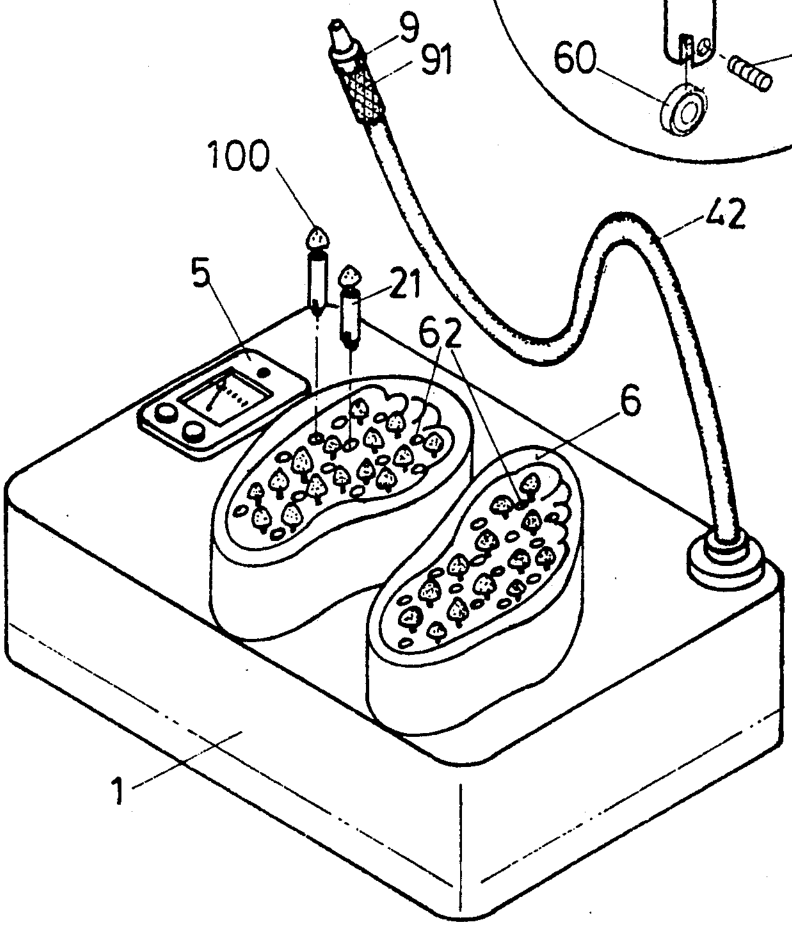
FIG. 5 is a perspective view of the massager of the invention.

The housing 1 consists of a base plate 11 and a cover portion 12. The foot receptacles 6 comprise a pair of walls integrally attached to the upper surface of the cover portion 12 and extending upwardly therefrom. The bottom walls or support portions of each foot receptacle 6 is provided with a plurality of guide openings 62 which correspond to accupressure points located in the sole of a human foot. A first plurality of through openings 64 is disposed in the support portion between adjacent guide openings 62. A compartment 7 is mounted to the undersurface of the cover portion 12. Compartment 7 comprises an open upper end, sidewalls affixed to the undersurface of the cover portion 12 and extending downwardly therefrom, and a bottom wall having a second plurality of through openings 65 which correspond in number to and are aligned with the first plurality of through openings 64 formed in the support portion of the foot receptacle 6. Compartment 7 is of the sealed type, that is, the sidewalls of the compartment 7 are sealingly affixed to the cover portion 12 and integrally or sealingly affixed to the bottom wall of the compartment 7. A plurality of tubular sleeve members 22 are mounted in compartment 7. Each sleeve member 22 has an upper end contiguously received within a respective opening of the first plurality of openings 64 formed in the support portions of the foot receptacles 6, and a lower end contiguously received within a respective opening of the second plurality of through openings 65 formed in the bottom wall of the compartment 7. An elongated rod member 21 is disposed in each sleeve member 22. Each rod member 21 has an upper end provided with a threaded shaft 211 and a lower end provided with an inverted U-shaped recess and a wheel member 60 rotatably mounted in the recess by a pin member 50. As shown in FIG. 3, a removable massage head 100 is threadably engaged with each threaded shaft 211 of rod members 21. Massage heads 100 engage respective accupressure points in the soles of the user's feet. Massage heads 100 may be made from natural stones, plastics, or any suitable material.

The drive means 3 comprises a motor 30, a variable speed transmission 31, and a disk member 8. As shown in FIG. 2, the motor 30 is directly coupled to the variable speed transmission 31. The disk member 8 is rotatably mounted to the transmission 31 by a shaft having a lower end rotatably mounted to the transmission 31 and an upper end mounted to an undersurface of the disk member 8. Disk member 8 has an upper surface provided with a plurality of ridges mounted equidistantly thereon. The wheel member 60 of each rod member 21 contiguously contacts the upper surface of the disk member 8.

The means for providing a therapeutic fluid to the compartment 7 and consequently to the foot receptacles 6 through the guide openings 62, and to the flexible conduit 42 includes a fluid container 4 mounted within housing 1. The fluid container 4 may be an evaporator. The fluid container 4 is mounted to a side of the base plate 11. A T-type conduit 41 has a first end fluidly connected to the fluid container 4, a second end fluidly connected to the compartment 7, and a third end fluidly connected to the flexible conduit 42. A therapeutic fluid contained within the fluid container 4 is dispensed through the conduit 41 to the compartment 7 and to the flexible conduit 42. Flexible conduit 42 is heat insulated and is provided with a heat insulated handle. Therapeutic fluid in compartment 7 flows through guiding holes 62 to stimulate the sole accupressure points located in the sole of the human foot. Likewise, therapeutic fluid dispensed through flexible conduit 42 may be directed to any part of the user's body to provide therapeutic effects.

Figure 6B:
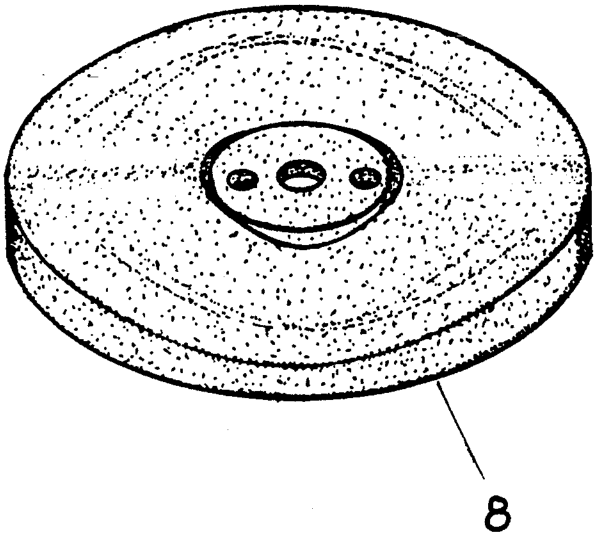
FIG. 6B is a perspective view of the disk with ridges of the invention.
Figure 6A:
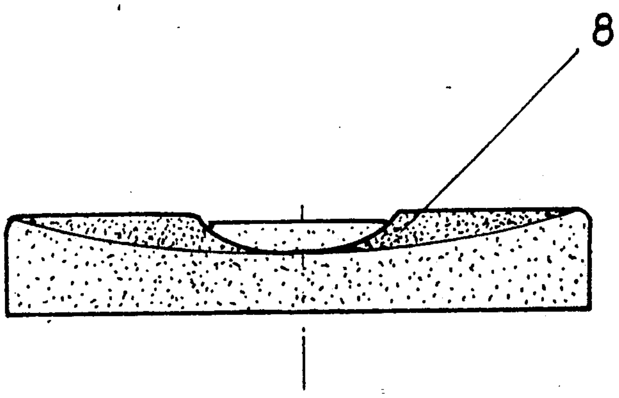
FIG. 6A is a cross-sectional view of the disk with ridges of the invention.

The means for controlling the drive means comprises a control panel 5 that controls the motor 30, the variable speed transmission 31, and a power source (not shown). The multi-point automatic sole massager can be activated by turning on a rocker switch on a control panel 5 to start the motor 30 and consequently to drive the variable speed transmission 31 and turn the disk 8, as shown in FIG. 6.

The rod members 21 are pushed upwardly by the ridges on the upper surface of the disk member 8, and move downwardly when not contiguously contacting the ridges to massage the respective accupressure points.

While the elongated rods are being moved up and down by the rotating disk 8, therapeutic fluid may be dispensed through the conduit 41 to the compartment 7 and eventually to the guiding holes 62 for moxibustion therapy simultaneously and/or separately.

The therapeutic fluid from the fluid container 4 can be dispensed to a moxibustion unit through a flexible conduit 42 simultaneously and/or separately for moxibustion therapeutic purposes at any other part of the user's body, while the user's feet are being massaged by the rod members 21 and the associated massaging heads 100.

While the invention has been described in connection with what are presently considered to be the most practical and preferred embodiment, it is to be understood that the invention is not limited to the disclosed embodiment, but, on the contrary, it is intended to cover various modifications and equivalent arrangements included within the spirit and scope of the appended claims.

I claim:

1. A multi-pointed automatic sole massager comprising:

a housing member having a base portion and a cover portion;

a plurality of continuous walls integrally attached to said cover portion and extending upwardly therefrom to form first and second receptacles adapted to receive a left and a right human foot, respectively, said first and second receptacles having support portions provided with a plurality of guide openings substantially corresponding to accupressure points on a sole of a human foot and a first plurality of through openings, each through opening being disposed between adjacent guide openings;

a compartment mounted to an interior surface of said cover portion, said compartment having an open upper end, sidewalls affixed to said interior surface of said cover portion and extending downwardly therefrom, and a bottom wall integrally attached to a lower end of each sidewall, said bottom wall having a second plurality of through openings, said second plurality of through openings corresponding to and being aligned with said first plurality of through openings formed in said support portions;

a drive means for rotating a disk member, said drive means being mounted in said housing and including a motor coupled to a variable speed transmission, and a shaft having a first end attached to said disk member, and a second end rotatably mounted to said variable speed transmission, said disk member having an upper surface provided with a plurality of ridges mounted equidistantly thereon;

a plurality of tubular sleeve members mounted in said compartment, each said sleeve member having upper and lower ends contiguously received within said first plurality of through openings formed in said support portions of said receptacles and said second plurality of said through openings formed in said bottom wall of said compartment, respectively;

a plurality of elongated rod members disposed within and extending through respective sleeve members, each said rod member having an upper end provided with a threaded shaft and a lower end provided with a wheel member rotatably mounted thereon, each said wheel member contiguously contacting said upper surface of said disk member;

a plurality of removable massage heads, each removable massage head being threadably engaged with a respective threaded shaft of said rod member;

an elongated flexible conduit attached to said cover portion of said base member;

means for supplying a fluid to said compartment and to said flexible conduit, said fluid supplying means being mounted to said housing; and, means for controlling said drive means, said controlling means being mounted to said housing member.

2. A multi-pointed automatic sole massager as recited in claim 1 wherein said fluid supplying means is an evaporator.

* * * * *